United States Patent [19]

Murawski et al.

[11] 4,033,336

[45] July 5, 1977

[54] SYSTEM FOR SENSING AND RECORDING MEDICAL INFORMATION

[75] Inventors: Frank H. Murawski, Tarpon Springs; James W. Elliott, Seminole; Fred W. Richards; Gordon L. Johns, both of Clearwater, all of Fla.

[73] Assignee: Medical Scientific International Corporation, Clearwater, Fla.

[22] Filed: Nov. 19, 1975

[21] Appl. No.: 633,411

[52] U.S. Cl. .................. 128/2.05 R; 33/174 D; 128/2 D; 128/2 S; 128/2.05 A; 128/2.06 B; 346/33 ME

[51] Int. Cl.² .................................. A61B 5/00

[58] Field of Search .......... 128/2 D, 2 F, 2 R, 2 S, 128/2.05 A, 2.05 M, 2.05 R, 2.06 B, 2.06 R, 2.1 A; 33/174 D; 346/33 ME

[56] References Cited

UNITED STATES PATENTS

| | | | |
|---|---|---|---|
| 2,660,165 | 11/1953 | Miller | 128/2.06 B |
| 3,374,461 | 3/1968 | Anderholm et al. | 128/2.05 Q |
| 3,857,383 | 12/1974 | Sommerfeld et al. | 128/2 D |
| 3,905,354 | 9/1975 | Lichowsky | 128/2.05 M |
| 3,934,267 | 1/1976 | Kosaka et al. | 128/2.06 G |

FOREIGN PATENTS OR APPLICATIONS 352,453   4/1961   Switzerland .................. 128/2.06 R Primary Examiner—William E. Kamm
Attorney, Agent, or Firm—Finnegan, Henderson, Farabow & Garrett

[57] ABSTRACT

A system for sensing and recording items of medical information relating to the human body includes a plurality of sensing devices responsive to various parameters associated with the human body for producing data signals determined by the sensed parameters, a code generator for producing different code signals indicative of the various parameters to be sensed, and a recorder for recording the code signals and data signals in a predetermined relationship on a recording medium. The system is embodied as an insurance data collection system for automatically measuring and recording such characteristics of the human body as height, weight, girth (waist and chest expansion), blood pressure and electrocardiogram test results on a magnetic tape cassette. In addition, an input arrangement is provided to allow the results of an independent test, e.g., a urine examination, to be recorded on the cassette.

8 Claims, 15 Drawing Figures

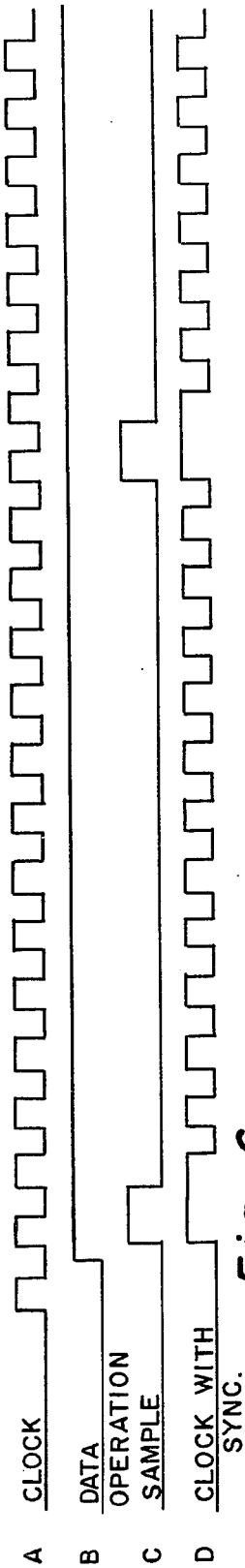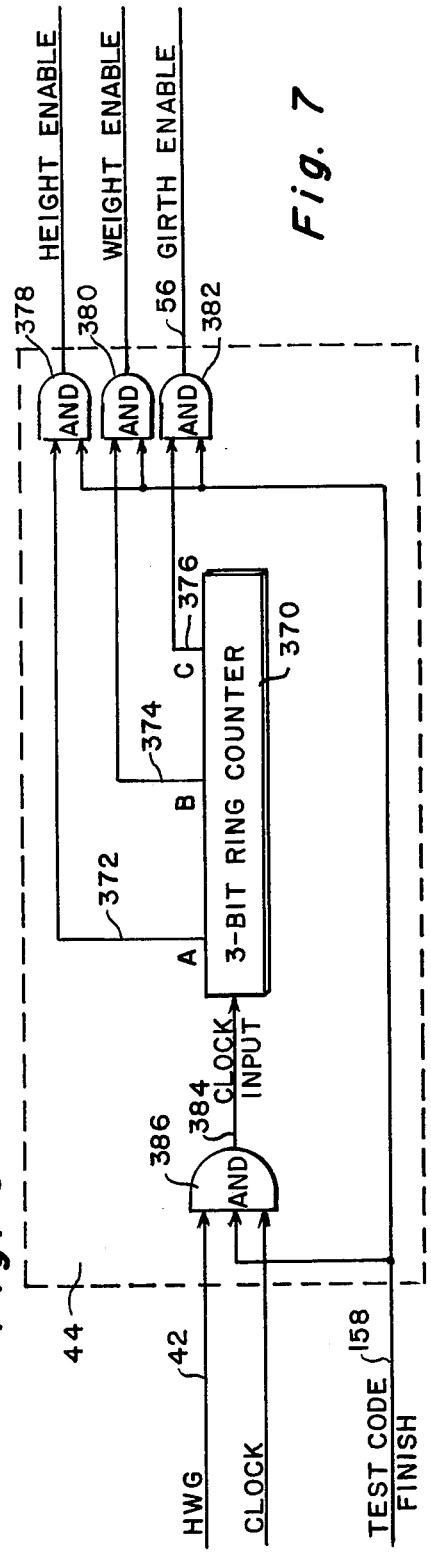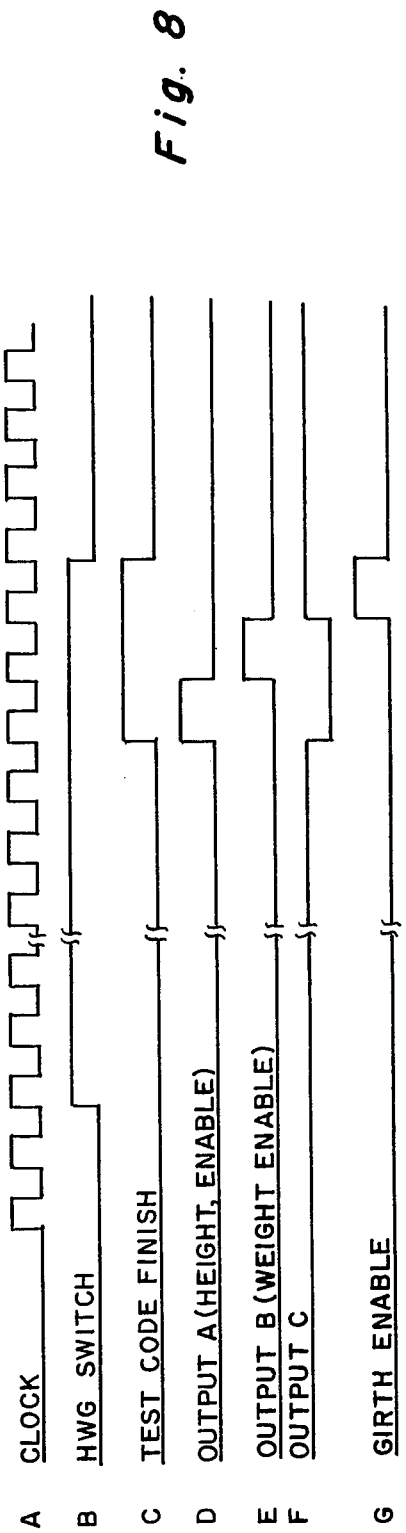

SYSTEM FOR SENSING AND RECORDING MEDICAL INFORMATION

The present invention relates to a system for sensing and recording various items of medical information relating to the human body on a recording medium and, more particularly, to an insurance data collection system for measuring and recording various characteristics of the human body, such as height, weight, girth, blood pressure, electrocardiogram test results and urine test results, on a magnetic tape cassette.

It has been customary in collecting relevant medical information in life insurance and health insurance evaluations to require a separate physical examination of a client applying for an insurance policy. The physical examination has usually been conducted in a separate visit to a physician or paramedic subsequent to an initial meeting with an insurance agent to discuss the client's medical history and other information relevant to the insurance policy. The inconvenience of a visit to a physician's office or paramedic facility for a physical examination has frequently discouraged clients from pursuing life and health insurance which they might otherwise have purchased.

Although systems have been previously proposed for collecting and recording medical data in connection with insurance evaluations, no previous system has incorporated the convenience and reliability of a magnetic tape cassette system. For example, it has been proposed to use a system in which medical information is recorded in analog form on a paper strip chart. However, such strip chart recorders have suffered from the disadvantage that the information record, i.e., the paper strip chart, is easily damaged. In addition, confidentiality of the information is difficult to protect because the medical information is readily observable on the strip chart. Further, since the medical data recorded on the strip chart is in analog form, the information is susceptible to misinterpretation and inaccuracy in transscribing the data into permanent insurance records.

The present invention achieves a system for sensing and recording items of medical information on a recording medium such as a magnetic tape cassette. A unique code is generated and recorded along with each item of medical information to identify the various types of medical information on the recording medium. In addition, the medical information and codes are preferably recorded in digital form to minimize the possibility of error in transcribing the information and to preserve the confidentiality of the information.

In accordance with the invention, a system for sensing and recording various items of medical information relating to the human body on a recording medium comprises means for sensing various parameters associated with the human body and producing corresponding data signals determined by the sensed parameters, means for generating different code signals indicative of the various parameters to be sensed, and means for recording the code signals and the data signals in a predetermined relationship on the recording medium. Preferably, the system includes a plurality of manually operable controls corresponding to the various parameters to be sensed for operating the code generating means to produce the different code signals indicative of the various parameters. The system may also include a plurality of prompt lights operable in succession to indicate a predetermined sequence of parameters to be sensed and recorded.

A preferred embodiment of the invention is embodied as a system for measuring and recording various items of medical information relating to the human body on a magnetic tape casette. The system comprises a plurality of measuring devices responsive to the various characteristics of the human body for producing analog data signals representative of the various characteristics, a plurality of manually operable controls corresponding to the measuring devices, control means including a test code generator responsive to actuation of the controls for producing different test code signals corresponding to the various measurements to be performed, an analog to digital converter for converting the test code signals and the analog data signals into digital code and data signals, respectively, multiplexer means responsive to the test code signals for selectively applying the analog data signals to the analog to digital converter, and means for recording the digital code and data signals produced by the analog to digital converter in a predetermined relationship on a magnetic tape cassette.

The preferred embodiment of the system may include an anthropometer for measuring height, weight and girth of the human body and producing analog signals representative of the magnitude of such measurements, a blood pressure monitor including a cuff and a microphone pickup mounted on the cuff for sensing the Korotkoff sounds prodced by pulsations of the bloodstream, and an electrocardiogram unit comprising a plurality of input electrodes for connection to the limbs and/or chest of the human body and a sensing circuit responsive to the input electrodes for providing the standard electrocardiogram leads. The preferred embodiment may also include a voice input arrangement to allow relevant information to be orally recorded.

The present invention provides a system for collecting medical information in connection with an insurance investigation which eliminates the need for a separate physical examination by a physician or paramedic. The system allows the necessary medical information to be conveniently and automatically recorded by a person with minumum training in the operation of the system. The medical information is rapidly and automatically recorded on a magnetic tape cassette. No disrobing is required. The use of a tape cassette system permits complete concealment of the medical data at the insurance field office.

The accompanying drawings illustrate a preferred embodiment of the invention and, together with the description, serve to explain the principles of the invention.

Of the drawing:

FIGS. 1 and 2 comprise a block diagram illustrating a system constructed in accordance with the principles of the present invention for sensing and recording various items of medical information relating to the human body on a recording medium, such as a magnetic tape cassette;

FIG. 6 illustrates waveforms associated with the operation of the various components of the analog to digital converter and clock and sync circuit of FIG. 5;

FIG. 7 is a more detailed circuit diagram of a sequential selection circuit incorporated in the system of FIG. 1;

FIG. 8 illustrates waveforms associated with the operation of the various components of the sequential selection circuit of FIG. 7;

Figure 1:
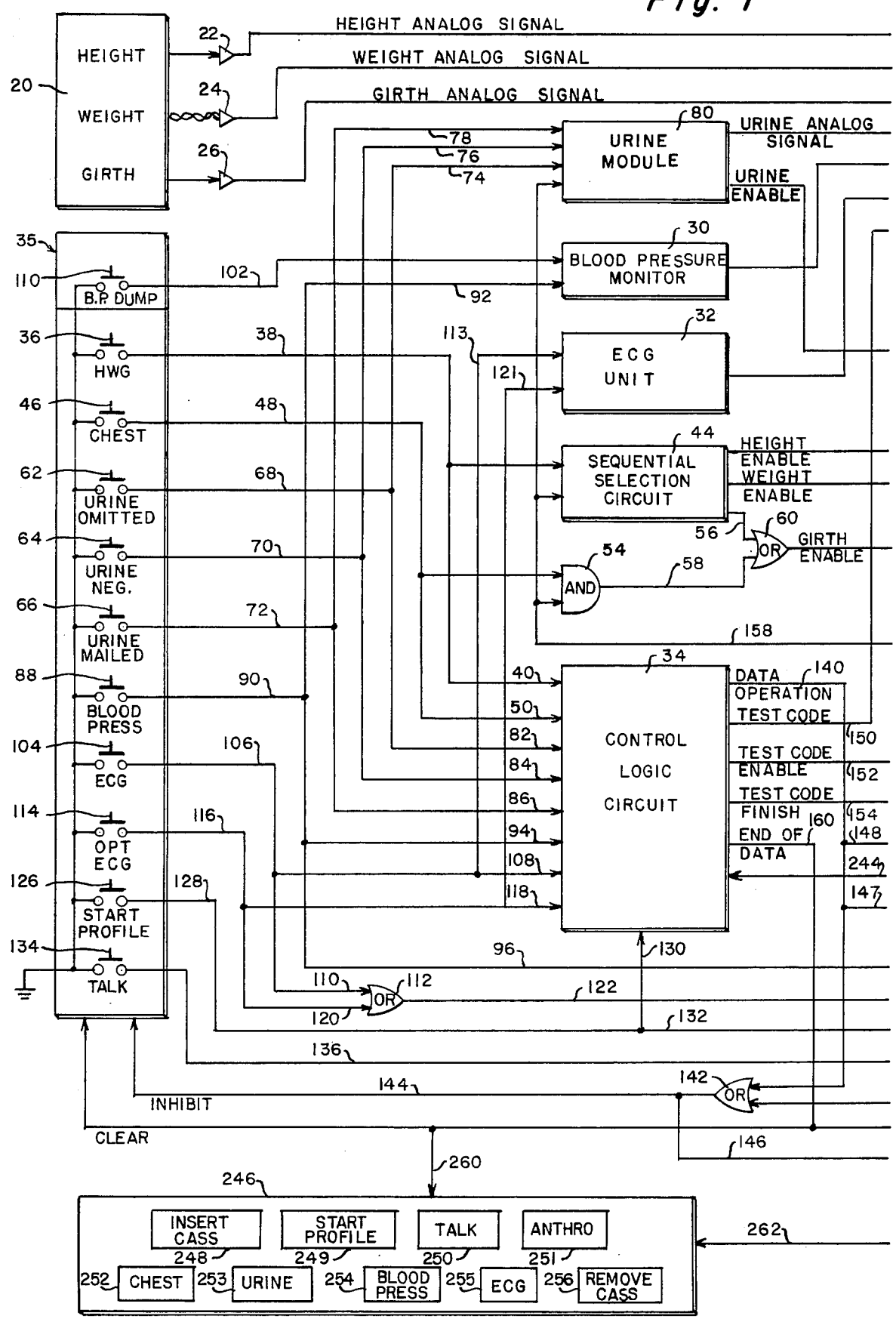
FIGS. 1 and 2 illustrate the basic components of a system for sensing and recording various items of medical information relating to the human body on a recording medium. Preferably, the system is arranged to record the information on a magnetic tape cassette.

In accordance with the invention, the system includes means for sensing various parameters associated with the human body and producing corresponding data signals determined by the sensed parameters. Preferably, the sensing means is embodied as a plurality of measuring devices responsive to various characteristics of the human body for producing analog data signals representative of the various characteristics. For example, as shown in FIG. 1., the system includes a body measuring unit 20, known as an anthropometer, for measuring height, weight, and girth of the human body and producing analog data signals which are representative of the magnitude of such measurements and are applied to buffer amplifiers 22, 24 and 26, respectively.

The sensing means may also include a blood pressure monitor 30 including an inflatable cuff and microphone (not shown) for sensing sounds produced by pulsations in the bloodstream and producing data signals corresponding to the sounds. In addition, the sensing means may include an electrocardiogram unit 32 including electrodes (not shown) to be attached to the human body for performing standard electrocardiogram readings on the human body and producing an ECG analog signal corresponding to each standard reading. The details of the blood pressure monitor and electrocardiogram unit are explained below.

In addition, in accordance with the present invention, the system includes means for generating different code signals indicative of the various parameters to be sensed. The generating means is embodied as a control logic circuit 34 (FIG. 1) which includes a test code generator for producing unique test code signals corresponding to the various measurements or tests to be performed. A more detailed description of the control logic circuit and test code generator appears below.

Preferably, the system includes a plurality of manually operable controls corresponding to the various parameters to be sensed for operating the code generating means to produce the unique code signals indicative of the various parameters. The controls are embodied as switch circuitry, generally 35, including a plurality of manually operable switches.

For example, a manually operable switch 36 (designated "HWG"), which corresponds to body measuring unit 20, is connected by a conductor 38 to an input line 40 of control logic circuit 34 and to an input line 42 of a sequential selection circuit 44 which sequentially produces enabling signals corresponding to the height, weight and girth measurements, respectively, performed by body measuring unit 20. In addition, a manually operable switch 46 (designated "CHEST") is connected by a conductor 48 to an input line 50 of control logic circuit 34 and to an input line 52 of a chest selection circuit comprising an AND gate 54. The girth output of sequential selection circuit 44 and the output of chest selection circuit 54 are applied by conductors 56 and 58, respectively, to an OR gate 60 to generate a "Girth Enable" signal.

In addition, a plurality of manually operable switches 62, 64 and 66 (labeled "URINE OMITTED," "URINE NEG" and "URINE MAILED"), is connected by conductors 68, 70 and 72 to input lines 74, 76 and 78, respectively, of a urine module 80. The purpose of switches 62, 64 and 66 and urine module 80 is to permit an operator to record the results of an indpendent test, e.g., a urine examination, not directly measured by the system. The urine module, which is explained in more detail below provides a urine analog signal indicative of the test results. Switches 62, 64 and 66 are also connected by conductors 68, 70 and 72 to input lines 82, 84 and 86, respectively, of control logic circuit 34.

Figure 2:
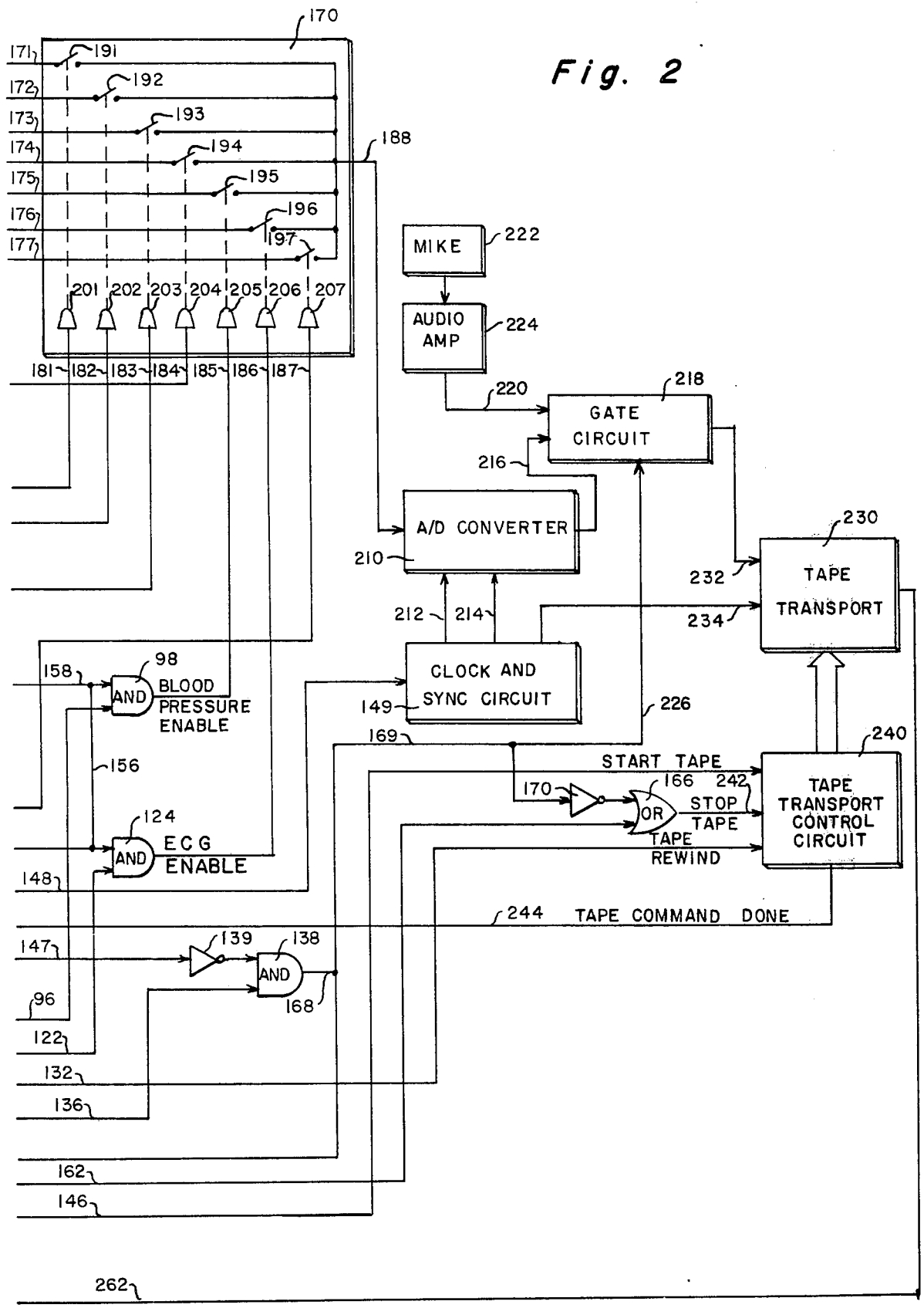

The controls also include a manually operable switch 88 (labeled "BLOOD PRESS") connected by a conductor 90 to an input line 92 of blood pressure monitor 30. Switch 88 is also connected by conductor 90 to an input line 94 of the control logic circuit and to an input line 96 of a blood pressure selector circuit comprising an AND gate 98 (FIG. 2).

As shown in FIG. 1, a manually operable switch 100 (labeled "B. P. DUMP") is connected by a conductor 102 to blood pressure monitor 30. The function of this switch is to allow the inflatable cuff of the blood pressure monitor to be rapidly deflated.

The controls also include a manually operable switch 104 (labeled "ECG") connected by a conductor 106 to an input line 108 of control logic circuit 34 and to an input 110 of an OR gate 112. ECG switch 104 is also connected via a conductor 113 to electrocardiogram unit 32. An additional manually operable switch 114 (labeled "OPT ECG") is connected by a conductor 116 to an input line 118 of the control logic circuit and to a second input 120 of OR gate 112. OPT ECG switch is also coupled via a conductor 121 to electrocardiogram unit 32. The output of OR gate 112 is connected by a conductor 122 to the input of an ECG selector circuit comprising an AND gate 124 (FIG. 2).

Further, as shown in FIG. 1, the controls include a manually operable switch 126 (labeled "START PROFILE") connected by a conductor 128 to provide an input signal to control logic circuit 34 via a conductor 130 to indicate the start of a test profile. In addition, switch 126 applies a "Tape Rewind" signal to a conductor 132.

Finally, the controls include a manually operable switch 134 (labeled "TALK") connected by a conductor 136 to a first input of an AND gate 138 (FIG. 2). An inverter 139 is connected to a second input of AND gate 138. The inverter and AND gate comprises a talk selector circuit which activates the system to respond to a voice input arrangement described in detail below.

Each of the switches of switch circuitry 35, with the exception of TALK switch 134, has an associated latch circuit (not shown) which is latched on when the corresponding switch is activated. For example, each of switches 36, 46, 62, 64, 66, 88, 104, 114, and 126 may be gated to a latching flip-flop by an appropriate gate. After one of the flip-flops is latched on by operation of the corresponding switch, the remaining switch circuits can be disabled by an appropriate inhibit signal applied to the gates. Only B.P. DUMP switch 100 is excluded from the inhibit arrangement to allow the pressure in the inflatable cuff of the blood pressure module to be released at any time. After the recording of data information is completed, the inhibit signal is removed and the flip-flop which was previously latched on is returned to its off condition by an appropriate clear signal applied to all of the flip-flops in the switch circuitry.

Only TALK switch 134 is not provided with any latching circuit. Consequently, to activate the voice recording arrangement, it is necessary for the operator to continuously depress the TALK switch.

Referring to FIG. 1, control logic circuit 34 includes a first output 140 (labeled "DATA OPERATION") which, in response to actuation of any one of switches 36, 46, 62, 64, 66, 88 104 and 114 provides an output signal to define a predetermined time interval for the processing of data information by the system. Output 140 of the control logic circuit is connected to a first input of an OR gate 142. The output of OR gate 142 provides an inhibit signal which is applied by a conductor 144 to the switch circuitry to inhibit actuation of all other switches except B.P. DUMP switch 100 during the processing of the selected data information. The output of OR gate 142 also applies a "Start Tape" signal to a conductor 146.

In addition, output 140 of the control logic circuit is connected by an input line 147 to inverter 139 (FIG. 2) to provide an inhibit signal to AND gate 138 to preclude operation of the voice recording arrangement during the processing of data information. Further, output 140 applies a start signal via a conductor 148 to a clock and sync circuit 149.

As shown in FIG. 1, control logic circuit 34 also includes a second output 150 (labeled "TEST CODE") to which the "Test Code" signals produced by the test code generator are applied. A third output 152 (labeled "TEST CODE ENABLE") produces a "Test Code Enable" signal for a predetermined time period.

A fourth output 154 (labeled "TEST CODE FINISH") produces an output signal upon termination of the "Test Code Enable" signal. The "Test Code Finish" signal produced at output 154 is used as an enable signal for AND gates 98 and 124, urine module 80, sequential selection circuit 44 and chest selection circuit 54. As shown in FIGS. 1 and 2, each of these circuits includes an enabling input coupled to output 154 of the control logic circuit via conductors 156 and 158.

Finally, the control logic circuit includes a fifth output 160 (labeled "END OF DATA") which generates a signal at a predetermined time after initiation of the "Test Code Finish" signal to terminate recording of data information from the selected sensing device. The "End Of Data" signal produced by the control logic circuit at output 160 is applied by a conductor 162 to the switch circuitry to clear all switches. In addition, the "End Of Data" signal is applied by a conductor 164 to a first input of an OR gate 166 (FIG. 2) to generate a "Stop Tape" signal. A second input of OR gate 166 is coupled by conductors 168 and 169 and an inverter 170 to the output of AND gate 138.

The test code and control signals produced by control logic circuit 34 and the analog data signals produced by the various measuring devices, e.g., body measuring unit 20, blood pressure monitor 30, and electrocardiogram unit 32, are applied to a multiplexer circuit 170 (FIG. 2). The multiplexer circuit includes a plurality of input lines 171–177 and a plurality of select lines 181–187 for selecting the input signal to be applied to an output 188 of the multiplexer. Input lines 171, 172 and 173 receive the height analog signal, weight analog signal, and girth analog signal, respectively, produced by buffer amplifiers 22, 24 and 26. Input line 174 receives the urine analog signal fro urine module 80. Input line 175 receives a blood pressure analog signal from the output of blood pressure monitor 30 and input line 176 receives the ECG analog signal from the output of electrocardiogram unit 32. Input line 177 is connected to output 160 of control logic circuit 34 to receive the "Test Code" signal produced by the test code generator. Select lines 181 and 182 receive "Height Enable" and "Weight Enable" signals, respectively, from sequential selection circuit 44. Select line 183 responds to the "Girth Enable" signal produced by OR gate 60, while select line 184 responds to a "Urine Enable" signal produced by urine module 80. Select lines 185 and 186 receive "Blood Pressure Enable" and "ECG Enable" signals from AND gates 98 and 124, respectively. Finally, select line 187 receives the "Test Code Enable" signal from output 152 of control logic circuit 34.

As shown in FIG. 2, multiplexer circuit 170 includes a plurality of normally open switches 191–197 coupled to input lines 171–177, respectively, with the switch outputs coupled in common to multiplexer output 188. The multiplexer circuit also includes a plurality of switch actuators 201–207, corresponding to switches 191–197 and connected to select lines 181–187, respectively, for closing the switches in response to enable signals applied to the select lines. Preferably, the multiplexer circuit is embodied as a solid-state semiconductor circuit.

The system also includes means for converting the analog data signals and the code signals into digital data signals and digital code signals, respectively. As shown in FIG. 2, this means is embodied as an analog to digital converter 210 havig its input coupled to output 188 of multiplexer 170 for converting the analog signals produced by the multiplexer into digital form. Converter 210 also receives sample and clock signals via conductors 212 and 214, respectively, from clock and sync circuit 149. The digital data signals produced by analog to digital converter 210 are applied by a conductor 216 to a first input of a gate circuit 218. The gate circuit includes a second input connected by a conductor 220 to a voice recording arrangement.

The voice recording arrangement comprises a microphone 222 coupled to the input of an audio amplifier 224. The amplifier output is coupled to the second input of gate circuit 218 by conductor 220.

Gate circuit 218 is provided with an enabling input coupled by a conductor 226 to conductor 169 for receiving control signals from AND gate 138.

When the system is recording data information, control logic circuit 34 produces a signal at its output 140 which is applied via conductor 147 to inverter 139 to provide an inhibit signal to AND gate 138 of the talk selector circuit. Since AND gate 138 is inhibited, it does not apply an enable signal to gate circuit 218. As a result, digital data and code signals applied to gate circuit 218 via conductor 216 are passed to the output of the gate circuit.

When the system is not recording data information, the "Data Operation" signal at output 140 of control logic circuit 34 is terminated to remove the inhibit signal applied to AND gate 138 by inverter 139. Consequently, voice recording can be achieved by actuation of TALK switch 134 to actuate AND gate 138 via conductor 136 to apply an enable signal via conductors 168, 169 and 226 to gate circuit 218. As a result, gate circuit 218 is activated to respond to the voice input on conductor 220 rather than the digital data and code signals on conductor 216.

Further, in accordance with the invention, the system includes means for recording the code signals and the data signals in a predetermined relationship on a recording medium. For example, the test code signals may be recorded prior to the data signals to identify the type of measurement or test result represented by the data signals. Preferably, the recording means is embodied as a magnetic tape cassette recording unit.

Figure 3:
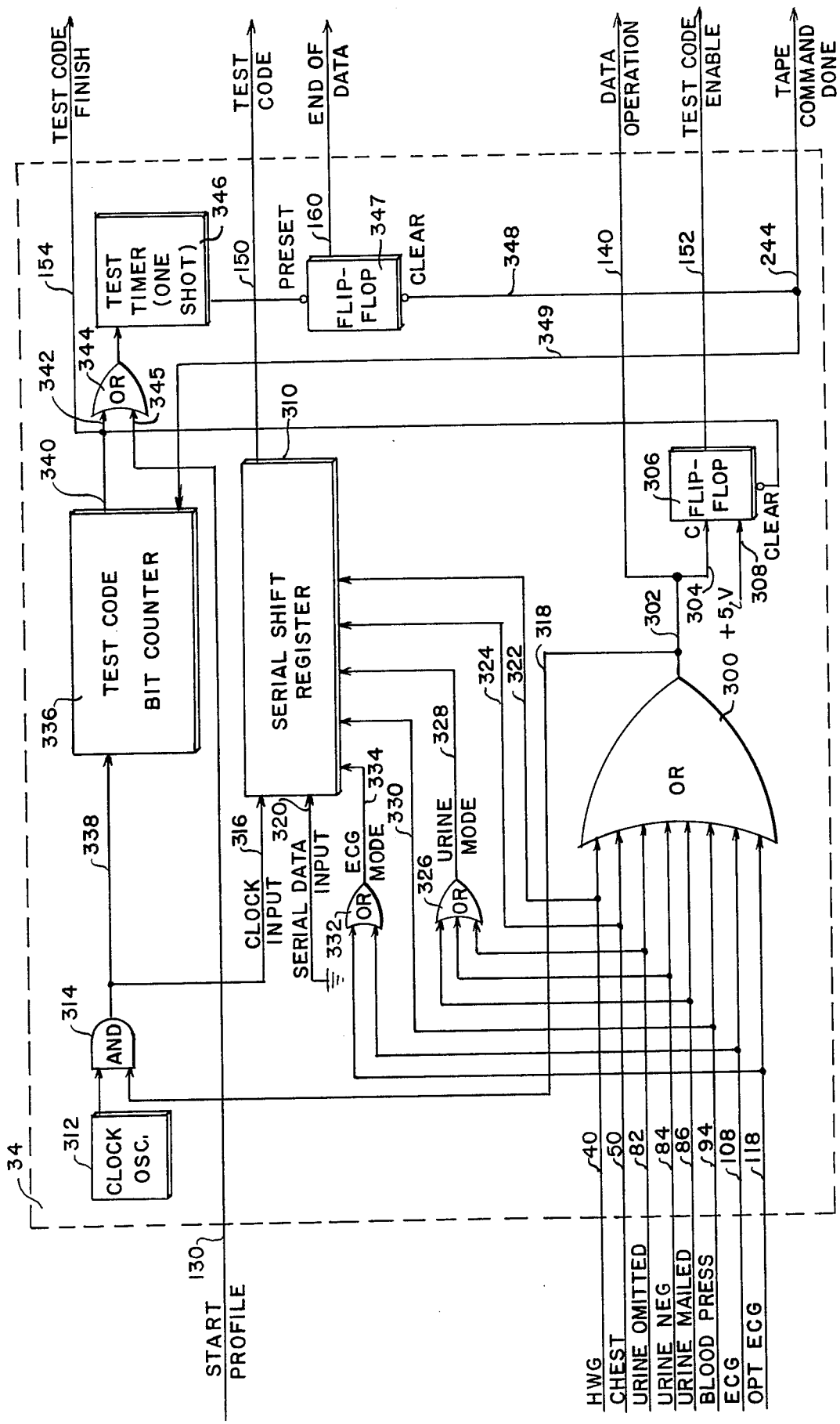
FIG. 3 is a more detailed circuit diagram of a control logic circuit incorporated in the system of FIG. 1 which includes a test code generator for producing unique test code signals corresponding to the various items of information to be recorded.

As shown in FIG. 3, the recording unit generally comprises a tape transport 230 for receiving a magnetic tape cassette (not shown) and recording input signals on the different channels of the tape cassette. For example, tape transport 230 includes a first input 232, corresponding to channel 1 of the cassette tape, for receiving digital data and code signals and voice input signals from gate circuit 218. In addition, the tape transport includes a second input 234, corresponding to channel 2 of cassette tape, for receiving clock and sync signals from clock and sync circuit 149.

As indicated in FIG. 2, tape transport 230 is operatively coupled to a tape transport control circuit 240. The tape transport control circuit includes a first input responsive to the "Start Tape" signal applied by OR gate 142 (FIG. 1) to conductor 146 to initiate movement of the magnetic tape. The tape transport circuit also includes a second input coupled by a conductor 242 to the output of OR gate 166 which responds to the "Stop Tape" signal generated by the OR gate to terminate movement of the magnetic tape. Further, tape transport control circuit 240 includes a third input coupled by conductors 128 and 132 to START PROFILE switch 126 to receive a "Tape Rewind" signal at the beginning of a series of tests. Upon completion of any instruction applied to its inputs, tape control circuit 240 produces a "Tape Command Done" signal at its output which is applied by a conductor 244 to indicate the completion of the command.

The system also includes a prompt light circuit, generally 246, including a plurality of prompt lights operable in succession to indicate a predetermined sequence of operations to be performed. Prompt light circuit 246 includes a prompt light 248 labeled "INSERT CASS" and prompt lights 249 and 250 labeled "START PROFILE" and "TALK," respectively. The prompt light circuit also includes prompt lights 251–255 labeled "ANTHRO," "CHEST," "URINE," "BLOOD PRESS," and "ECG:", respectively, which correspond to the various characteristics of the human body to be sensed and recorded. In addition, the prompt light circuit includes a prompt light 256 labeled "REMOVE CASS."

Prompt light circuit 246 includes a first input connected by a conductor 260 to conductor 162 to respond to the "End Of Data" signal generated at output 160 of control logic circuit 34. In addition, the prompt light circuit includes a second input connected by a conductor 262 to a microswitch (not shown) of tape transport 230 which senses whether a tape cassette is present in the tape transport.

Prompt light circuit 246 includes circuitry (not shown) to operate the prompt lights in succession to indicate a preferred sequence of stops to be followed by the operator. However, the prompt light circuit is only intended to provide a suggestion to the operator of the test sequence to be performed and it does not require the tests to be performed in any particular sequence. The circuitry allows the operator to perform any measurement or test desired and, upon completion of the measurement or test, activates the prompt light corresponding to the next measurement or test in the sequence.

OVERALL OPERATION

The operator interfaces with the system by control switch circuitry 35 and prompt light circuit 246. The prompt lights are used to indicate to the operator the desired sequence of operations to be performed. However, the operator is not required to conduct the prompted measurement or test and may conduct any operation desired.

Initially, when the system is not in use, i.e., with no cassette in tape transport unit 230, prompt light 248 is illuminated to indicate that insertion of a tape cassette is required. When a tape cassette is inserted into the tape transport unit, prompt light 248 is extinguished and START PROFILE prompt light 249 is illuminated. At this point, the operator actuates START PROFILE switch 126 to apply a start signal to control logic circuit 34 via conductors 128 and 130 and a "Tape Rewind" signal to tape transport control circuit 240 via conductor 132. As a result, tape transport 230 rewinds the tape cassette to the start position of its tape.

After the tape cassette is rewound, tape transport control circuit 240 applies a control signal for a predetermined time to tape transport 150 to advance the leader at the beginning of the tape past the record heads of the tape transport prior to recording of any test code or data signals. Simultaneously, if desired, a clock preamble signal, i.e., a series of clock pulses, may be recorded on the tape.

Upon completion of the initial rewinding operation and the recording of the clock preamble signal, tape transport control circuit 240 produces a "Tape Command Done" signal which is applied to control logic circuit 34 by conductor 244. This signal initiates an "End of Data" signal at output 160 of the control logic circuit which applies a control signal to prompt light circuit 250 to extinguish the START PROFILE prompt light and to illuminate TALK prompt light 250.

When TALK prompt light 251 is illuminated, the operator may activate the voice recording arrangement by actuation of TALK switch 134. The actuation of TALK switch 134 applies an input signal via conductor 136 to AND gate 138 which is enabled via inverter 139 by virtue of the absence of the "Data Operation" signal at output 140 of control logic circuit 34. The enabled AND gate applies a control signal via conductors 168, 169 and 226 to gate circuit 218 to disable the gate input connected to analog to digital converter 210 and enable the gate input coupled to conductor 220 to respond to the voice input arrangement comprising microphone 222 and auido amplifier 224. The control signal produced by AND gate 138 also initiates movement of the tape cassette. Since gate circuit 218 is enabled to apply voice signals to input 232 of tape transport 230, the operator can orally record any information pertinent to the test profile. In addition, the control signal produced by AND gate 138 is applied to OR gate 142 (FIG. 1) to inhibit actuation of the other control switches of switch circuitry 35.

Preferably, switch circuitry 35 requires the operator to continuously actuate TALK switch 134 to activate the voice recording arrangement. When the TALK switch is released, the control signal produced by AND gate 138 is terminated. By termination of this control signal, gate circuit 218 is returned to its normal condition in which the voice input arrangement is disabled and the gate input coupled to conductor 216 is enabled to receive digital signals from analog to digital converter 210. Simultaneously, a "Stop Tape" signal is applied to tape transport control circuit 240 to terminate movement of the tape cassette. Thereafter, the tape transport control circuit produces a "Tape Command Done" signal which is applied via conductor 244 to control logic circuit 34. The control logic circuit produces an "End Of Data" signal which is applied to prompt light circuit 246 via conductor 260 to extinguish TALK prompt light 250 and illuminate ANTHRO prompt light 251.

When ANTHRO prompt light 251 is illuminated, the operator sets up body measuring unit 20, as explained below, to perform height, weight and girth (e.g., waist) measurements on the client. Then, the operator actuates HWG switch 36 to actuate input 40 of control logic circuit 34. As a result, the control logic circuit produces a "Data Operation " signal at its output 140 to activate clock and sync circuit 149 and to apply a "Start Tape" signal to tape transport control circuit 240. In addition, OR gate 142 produces an inhibit signal which prevents actuation of any other control switch.

Control logic circuit 34 simultaneously produces a "Test Code" signal at its output 150, which is applied to input line 177 of multiplexer 170, and a "Test Code Enable" signal at its output 152, which is applied to select line 187 of the multiplexer. Upon actuation of select line 187, switch 197 (FIG. 2) in the multiplexer circuit is closed to allow the "Test Code" signal on input line 177 to pass to output 188 of the multiplexer. Analog to digital converter 210 converts the "Test Code" signal into a digital code signal which is applied to gate 218 and is recorded on channel 1 of the magnetic tape cassette.

After a predetermined time, the "Test Code Enable" signal is terminated to return switch 197 of the multiplexer to its normal, open condition and a "Test Code Finish" signal is produced at output 154 of the control logic circuit to enable sequential selection circuit 44. The sequential selection circuit initially produces a "Height Enable" signal which is applied to select line 181 to close switch 191 in multiplexer 170 to allow the height analog signal applied to input line 171 of the multiplexer to pass to its output 188. Analog to digital converter 210 converts the height analog signal into a digital data signal which is passed through gate 218 and recorded on channel 1 of the tape cassette. Subsequently, the "Height Enable" signal produced by sequential selection control circuit 44 is terminated to return multiplexer switch 191 to its initial, open condition, and a "Weight Enable" signal is applied to select line 182 to close multiplexer switch 192 and pass the weight analog signl applied to input line 172 to the multiplexer output. The weight analog signal is also converted into a digital data signal and recorded on channel 1 of the tape cassette. Thereafter, the "Weight Enable" signal is terminated to return switch 192 to its intial, open position.

Finally, sequential selection circuit 44 applies a control signal to OR gate 60 via conductor 56 to produce a "Girth Enable" signal which is applied to select line 183 to close multiplexer switch 193 and pass the girth analog signal applied to input line 173 to the multiplexer output. The girth analog signal is also converted into a digital data signal which is recorded on channel 1 of the tape cassette.

After a predetermined time, control logic circuit 34 generates an "End of Data" signal at its output 160 which is applied by conductor 164 to OR gate 166 to apply to "Stop Tape" command to tape transport control circuit 240 to terminate motion of the tape casette. In addition, the "End Of Data" signal is used to clear the switch circuitry and to extinguish prompt light 251 and to illuminate CHEST prompt light 252. When the motion of the tape cassette is terminated, the tape transport control circuit transmits a "Tape Command Done" signal to control logic circuit 34 via conductor 244 to terminate the "End of Data" and "Test Code Finish" signals.

Thereafter, the operator can perform a chest expansion measurement by arranging body measuring unit 20 to sense the chest expansion of the client and actuation CHEST switch 46 to apply a control signal to input 50 of control logic circuit 34. As a result, the control logic circuit initially generates a "Data Operation" signal at its output 140 to initiate movement of the tape cassette and inhibit the other control switches. The control logic circuit also generates a "Test Code" signal at its output 150 which uniquely identifies the chest expansion measurement and a "Test Code Enable" signal which is applied to select line 187 of the multiplexer circuit. As a result, multiplexer switch 197 is again closed to allow the "Test Code" signal to pass through the multiplexer for conversion into a digital code signal and recording on channel 1 of the tape cassette.

After a predetermined time, the "Test Code Enable" signal is terminated to return multiplexer switch 197 to its normal, open condition and a "Test Code Finish"-'signal is generated at output 154 of the control logic circuit to enable the chest selection circuit, i.e., AND gate 54, which applies a control signal via conductor 58 to OR gate 60 to generate a "Girth Enable" signal. This signal is applied to select line 183 to close multiplexer switch 193 and allow the girth analog signal at input 173 to pass through the multiplexer for conversion into a digital data signal which is recorded on channel 1 of the tape cassette. After another predetermined time, the control logic circuit generates an "End Of Data" signal at its output 160 to actuate OR gate 166 to apply a "Stop Tape" command to tape transport control circuit 240 to stop the tape cassette. As a result, the switch circuitry is cleared, prompt light 252 is extinguished and URINE prompt light 253 is illuminated. Upon termination of the motion of the tape cassette, tape transport control circuit 240 transmits a "Tape Command Done" signal to the control logic circuit via conductor 244 to terminate the "Test Code Finish" and "End Of Data" signals.

At this point, the operator may perform a test on a urine sample taken from the client. If the test results are negative, the operator actuates control switch 64. If the test is positive, the operator actuates control switch 66 and forwards the urine sample along with the other recorded test results for further evaluation. If the urine test is omitted, the operator actuates control switch 62.

The actuation of any one of switches 62, 64 and 66 results in the production of "Data Operation", "Test Code" and "Test Code Enable" signals at outputs 140, 150 and 152, respectively, to start the tape cassette and to record a unique digital code signal on channel 1 of the cassette. The same test code signal is generated regardless of whether switch 62, 64 or 66 is actuated.

Upon termination of the "Test Code Enable" signal, control logic circuit 34 generates a "Test Code Finish" signal to enable urine module 80. The urine module produces a urine analog signal having a voltage level determined by which one of control switches 62, 64 and 66 is actuated. In addition, urine module 80 produces a "Urine Enable" signal which is applied to select line 184 to close multiplexer switch 194 to permit the urine analog signal to pass to multiplexer output 188 for conversion into a digital data signal and recording on channel 1 of the tape cassette. After a predetermined time, the "End Of Data" signal appears at output 160 of the control logic circuit to stop the tape cassette and clear the switch circuitry. Thereafter, upon receipt of a tape command done signal from the tape transport control circuit, control logic circuit 34 terminates the "Test Code Finish" signal and "End Of Data" signal at its outputs 154 and 60, respectively. Consequently, prompt light 253 is extinguished and BLOOD PRESS prompt light 254 is illuminated.

AT this point, the operator activates control switch 88 to apply a control signal to input line 94 to activate control logic circuit 34 and to initiate inflation of the inflatable cuff of blood pressure monitor 30. The control logic circuit again starts the tape cassette and initiates a unique "Test Code" signal which is recorded on channel 1 of the tape cassette to identify a blood pressure measurement. Upon termination of the "Test Code Enable" signal the control logic circuit generates a "Test Code Finish" signal at its output 154 to enable AND gate 98. Since BLOOD PRESS switch 88 is activated, AND gate 98 is activated by conductor 96 to produce a "Blood Pressure Enable" signal which is applied to select line 185 to close multiplexer switch 195 and allow the blood pressure analog signal applied to input line 175 by blood pressure monitor 30 to pass to the multiplexer output. The blood pressure analog signal is converted into a digital data signal and recorded on channel 1 of the tape cassette.

When the inflatable cuff of blood pressure monitor 30 is deflated to a predetermined pressure, the control logic circuit generates an "End of Data" signal to stop the tape cassette and clear the switch circuitry. Thereafter, a "Tape Command Done" signal from transport control circuit 240 terminates the "Test Code Finish" signal and "End of Data" signal at outputs 154 and 160 of the control logic circuit. Consequently, prompt light 254 is extinguished and ECG prompt light 255 is illuminated.

Upon illumination of prompt light 255, the operator actuates ECG control switch 104 to apply a control signal to input lne 108 to activate control logic circuit 34 to start the tape cassette and record an unique "Test Code" signal on channel 1 of the tape cassette to identify an ECG reading. When the "Test Code Enable" signal and output 152 of the control logic circuit is terminated, a "Test Code Finish" signal is generated at output 154 to enable AND gate 124. Since ECG control switch 104 is closed, OR gate 112 applies a control signal to AND gate 124 to produce an "ECG Enable" signal which is applied to select line 186 to close multiplexer switch 196 to allow the ECG analog signal applied to input line 176 from ECG module 32 to pass to multiplexer output 188. The ECG analog signal is converted into a digital data signal and recorded on channel 1 of the tape cassette.

After a predetermined time, the "End Of Data" signal at output 160 of the control logic circuit is terminated to stop the tape cassette and clear the switch circuitry. Upon receipt of a "Tape Command Done" signal from tape transport control circuit 240, control logic circuit 34 terminates the "Test Code Finish" signal and "End Of Data" signal at outputs 154 and 160. Consequently, prompt light 255 is extinguished and TALK prompt light 256 is illuminated.

CONTROL LOGIC CIRCUIT

Referring to FIG. 3, control logic circuit 34 includes an OR gate 300 having a plurality of inputs connected to input lines 40, 50, 82, 84, 86, 94, 108 and 118 which respond to the switch inputs designated "HWG," "CHEST," "URINE OMITTED," "URINE NEG," "URINE MAILED," "BLOOD PRESS"), "ECG" and "OPT ECG." OR gate 300 has an output 302 connected to output 140 of the control logic circuit to provide the "Data Operation" signal. In addition, the output of OR gate 300 is connected by a conducotr 304 to the clock input of a flip-flop 306. One data input of flip-flot 306 is connected by a conductor 308 to a DC potential source ($t5V$). The output of flip-flop 306 is connected to output 152 of the control logic circuit to provide the "Test Code Enable" signal.

The control logic circuit includes a test code generator responsive to actuation of the manually operable controls for producing different test code signals corresponding to the various measurements to be performed. The test code generator is embodied as a serial shift register 310 which is driven by a clock oscillator 312 coupled by an AND gate 314 to a clock input 316 of the shift register. The output of OR gate 300 is connected to a conductor 318 to apply an enable input to AND gate 314 upon actuation of any one of the manually operable controls connected to the input lines of the OR gate. A data input 320 of serial shift register 310 is grounded. The output of serial shift register 310 is coupled to output line 150 of the control logic circuit to produce the "Test Code" signal.

Serial shift register 310 is preset by actuation of the manually operable controls to produce different test code signals corresponding to the various measurements to be performed. For example, input line 40, which is coupled to HWG switch 36, is connected by a conductor 322 to a control input of a first stage of shift register 310 to program the shift register to produce a unique "Test Code" signal upon actuation of the HWG switch. Similarly, input line 50, which is coupled to CHEST switch 46, is connected by a conductor 324 to the control input of a second stage of shift register 310 to preset the register to produce another unique "Test Code" signal upon actuation of the CHEST switch.

In addition, input line 82, 84 and 86, which are coupled to URINE OMITTED switch 62, URINE NEG switch 64 and URINE MAILED switch 66, are connected to the inputs of an OR gate 326 having its output connected by a conductor 328 to the control input of a third stage of serial shift register 310. Upon actuation of any one of the switches 82, 84 and 86, OR gate 326 produces an output signal to preset shift register 310 to produce a unique "Test Code" signal to indicate the performance of an urine analysis.

Input line 94, which is coupled to BLOOD PRESS switch 88, is connected by a conductor 330 to a fourth stage of serial shift register 310 to preset the register to produce a unique "Test Code" signal upon actuation of the switch to indicate the measurement of blood pressure.

Input lines 108 and 118, which are coupled to ECG switch 104 and OPT ECG switch 114, respectively, are coupled to the inputs of an OR gate 332 having its output coupled by a conductor 334 to a fifth stage of serial shift register 310. Upon actuation of either switch 104 and 114, OR gate 332 produces an output signal to preset shift register 310 to produce a unique "Test Code" signal to indicate the performance of an electrocardiogram test.

Control logic circuit 34 also includes a test code bit counter 336, e.g., a binary ripple counter, having an input 338 driven by clock oscillator 312 through AND gte 314. The test code bit counter includes an output 340 coupled to output line 154 of the control logic circuit to produce the "Test Code Finish" signal. In addition, output 340 of the test code counter is coupled to a first input 342 of an OR gate 344. The OR gate includes a second input 345 connected to input line 130 of the control logic circuit which is coupled to START PROFILE switch 126. The output of OR gate 344 is connected to a test timer 346, i.e., a one-shot or monostable multi-vibrator, which is coupled to the preset input of a flip-flop 347. The output of flip-flop 347 is coupled to line 160 of the control logic circuit to produce the "End Of Data" signal.

Flip-flop 347 includes a clear input connected by a conductor 348 to conductor 244 to receive the "Tape Command Done" signal from the tape transport control circuit. In addition, test code bit counter 336 includes a clear input coupled to conductor 244 by a conductor 349.

When START PROFILE switch 126 (FIG. 1) is actuated, a control signal is applied via conductors 128 and 130 to control logic circuit 34. The control signal is also applied via conductor 132 (FIG. 2) as a "Tape Rewind" signal to tape transport control circuit 240 to initiate preliminary operations described above.

Referring to FIG. 3, the control signal on conductor 130 is applied to OR gate 344 to initiate operation of test timer 346. After a predetermined time period. test timer 346 applies a preset signal to flip-flop 347 to produce an "End Of Data" signal at output 160 of the control logic circuit. The "End Of Data" signal is used to clear switch circuitry 35 and to apply a "Stop Tape" command to tape transport control circuit 240. When the movement of the tape cassette is terminated, the tape transport control circuit produces a "Tape Command Done" signal which is applied to conductors 244 and 348 to clear flip-flop 347 and terminate the "End Of Data" signal.

Figure 4:
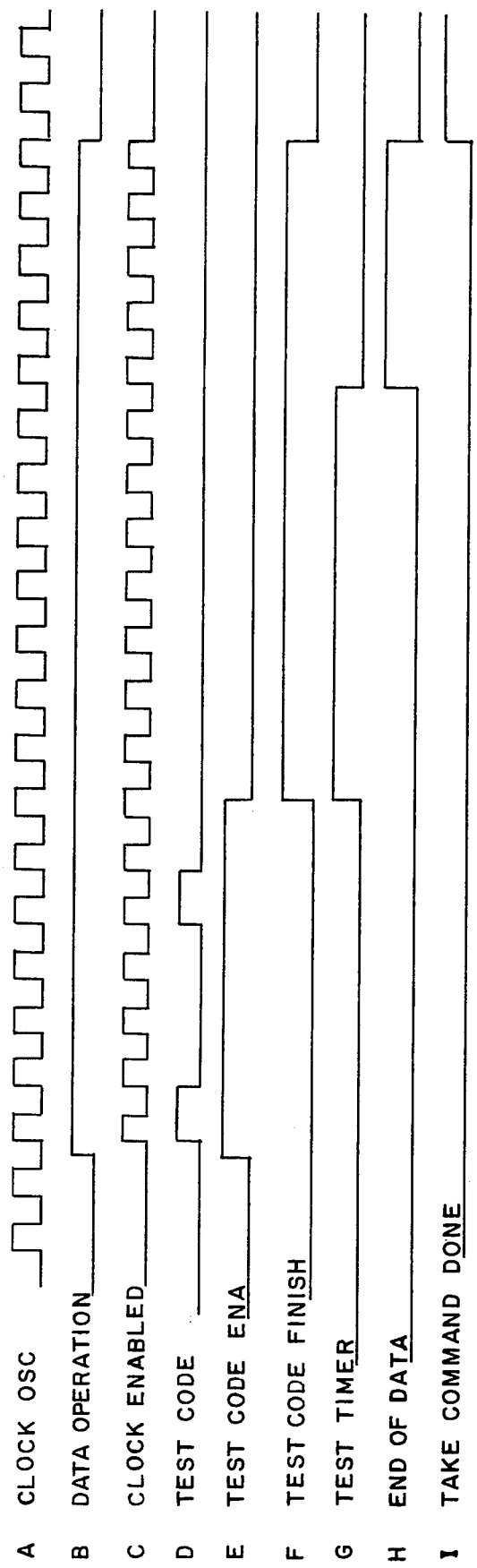
FIG. 4 illustrates the waveforms associated with the operation of the various components of the control logic circuit of FIG. 3.

When one of the manually operable controls coupled to input lines 40, 50, 82, 84, 86, 94, 108 and 118 is actuated, an appropriate control signal is applied to serial shift register 310 to present the shift register to produce a unique "Test Code" signal corresponding to the measurement or test to be performed. In addition, OR gate 300 produces an output signal (FIG. 4, line B) which indicates the initiation of a data operation. As illustrated in FIG. 4, line C, the output signal produced by OR gate 300 also enables AND gate 314 to pass the clock pulses (FIG. 4, line A) produced by clock oscillator 312. The clock pulses drive serial shift register 310 to produce a unique pulse arrangement (FIG. 4, line D) which constitutes the "Test Code" signal to identify the type of measurement or test, e.g., blood pressure, to be perfo.

In addition, as shown in FIG. 4, line E, the output signal produced by OR gate 300 sets flip-flop 306 to produce a "Test Code Enable" signal which continues for a time period determined by test code bit counter 336. The "Test Code" signal (FIG. 4, line D) is produced within the pulse width of the "Test Code Enable" signal (FIG. 4, line E). When test code bit counter 336 arrives at its predetermined count, the counter produces an output signal (FIG. 4, line F) which constitutes the "Test Code Finish" signal. This signal is applied to reset flip-flop 306 and terminate the "Test Code Enable" signal (FIG. 4, line E).

Referring to FIG. 3, the output signal of test code bit counter 336 is applied to OR gate 340 to initiate operation of test timer 346. As indicated in FIG. 4, line G, the test timer produces an output signal having a predetermined pulse width during which test data is recorded. At the end of the pulse (FIG. 4, line G) produced by test timer 346, flip-flop 348 is preset to produce the "End Of Data" signal (FIG 4, line H). Thereafter, upon receipt of a "Tape Command Done" signal (FIG. 4, line I) from the tape transport control circuit, flip-flop 348 is cleared to terminate the "End Of Data" signal (FIG. 4, line H). Upon termination of the "End Of Data" signal, the switch control circuitry is cleared and the "Test Code Finish" signal and "Data Operation" signal are terminated.

ANALOG TO DIGITAl CONVERTER ANd CLOCK AND SYNC CIRCUIT

Figure 5:
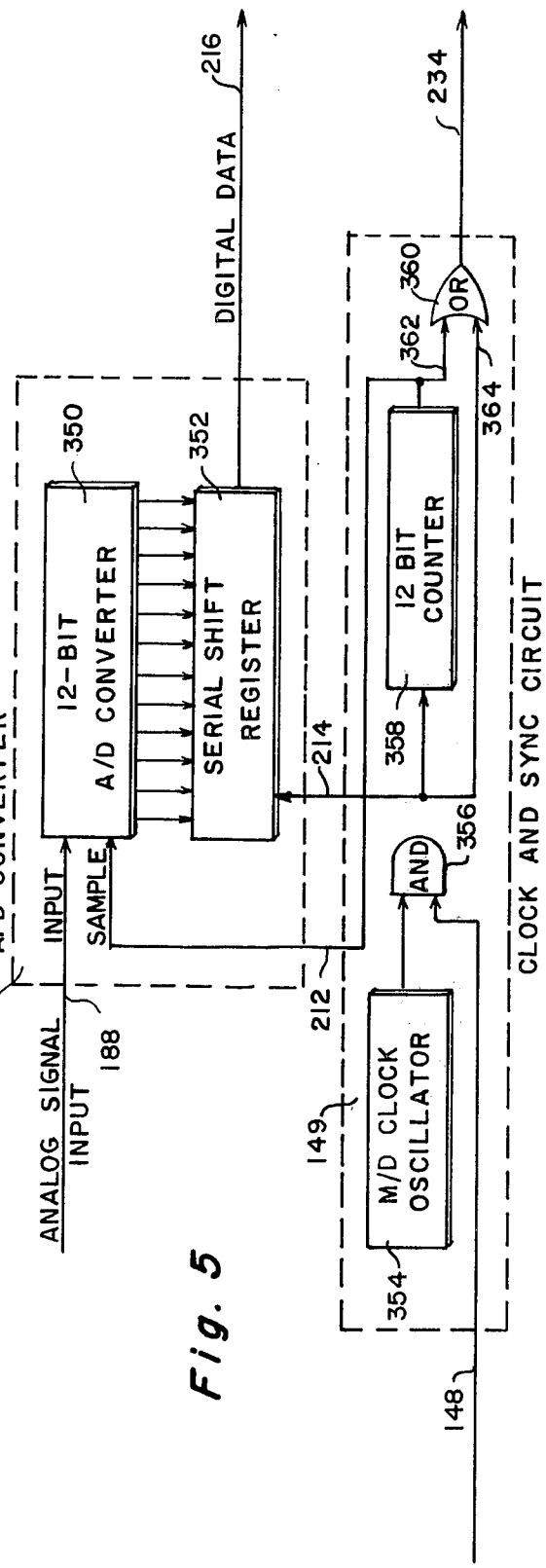
FIG. 5 is a more detailed circuit diagram of an analog to digital converter and a clock and sync circuit incorporated in the system of FIG. 1.

Referring to FIG. 5, analog to digital converter 210 is embodided as a twelve-bit analog to digital converter 350 including a series of 12 stages connected in parallel with corresponding stages of a serial shift register 352. A data input of analog to digital converter 350 is connected to output 188 of multiplexer circuit 170 (FIG. 2) to receive the analog signals produced by the multiplexer circuit. A sample input signal is applied to the analog to digital converter via conductor 212 from clock and sync circuitry 149. A clock input signal is applied to shift register 352 via conductor 214 to serially output the digital data stored in the shift register.

Clock and sync circuit 149 includes a clock oscillator 354 coupled to a first input of an AND gate 356 to drive a twelve-bit counter 358 coupled to the output of the AND gate. A second input of AND gate 356 is enabled by the "Data Operation" signal produced by control logic circuit 34 and applied to conductor 148. The enabled clock output produced by AND gate 356 is applied by conductor 214 as the clock input signal to serial shift register 352. The output of counter 358 is applied by conductor 212 as a sample input signal to analog to digital converter 350.

In addition, the clock and sync circuit includes an OR gate 360 having a first input 362 coupled to the output of counter 358 and a second input 364 coupled to the output of AND gate 356. The output of OR gate 360 is applied to conductor 234 to provide a "Clock With Sync" signal.

As shown in FIG. 6, line A, clock oscillator 354 continuously generates a series of uniformly spaced clock pulses. Upon application of a "Data Operation" signal (FIG. 6, line B) to conductor 148, AND gate 356 passes the clock pulses from clock oscillator 354 to apply the clock pulses to serial shift register 352 and counter 358. The counter periodically produces a sample output pulse (FIG. 4, line C) for every 12 clock pulses applied to the counter. OR gate 360 combines the sample output pulses from counter 358 and the clock pulses from AND gate 356 to produce the "Clock With Sync" signal (FIG. 4, line D).

In addition, the sample pulses (FIG. 4, line C) are used to actuate analog to digital converter 350 to periodically sample the analog input signal at output 188 of the multiplexer. The analog to digital converter transforms the analog signal produced by the multiplexer into a 12-bit character which is applied to serial shift register 352. The clock pulses applied to shift register 342 via conductor 214 serially shift the bits through the register to produce a 12-bit digital data signal on conductor 216 determined by the analog input signal from the multiplexer circuit.

SEQUENTIAL SELECTION CIRCUIT

As shown in FIG. 7, sequential selection circuit 44 includes a three-bit ring counter 370 having outputs A, B and C coupled by conductors 372, 374 and 376, respectively, to AND gates 378, 380 and 382, respectively. The counter also includes a clock input coupled by a conductor 384 to the output of an AND gate 386. The "Test Code Finish" signal applied by the control logic to conductor 158 is used as an enable signal for AND gates 378, 380, 382 and 386. AND gate 378 produces the "Height Enable" signal, while AND gate 380 produces the "Weight Enable" signal. The output of AND gate 382 is applied by conductor 56 to OR gate 60 (FIG. 1) to produce the "Girth Enable" signal. AND gate 386 includes an input connected to input line 42 which is coupled to HWG switch 36. In addition, AND gate 386 includes a clock input driven by clock oscillator 312 (FIG. 3) of the control logic circuit.

Referring to FIGS. 7 and 8, the application of clock pulses (FIG. 8, line A) to the clock input of ring counter 370 is initiated upon actuation of HWG switch 36 (FIG. 8, line B) and the occurrence of a "Test Code Finish" signal (FIG. 8, line C). Initially, as shown in FIG. 8, line D, ouput A of ring counter 370 is actuated to apply a pulse to AND gate 378 to produce the "Height Enable" signal. Next, a pulse is produced at output B of the counter (FIG. 8, line E) and applied to AND gate 380 to produce the "Weight Enable" signal. Finally, a pulse (FIG. 8, line F) is produced at output C of the counter and applied to AND gate 382 to generate the "Girth Enable" signal (FIG. 8, line G) at the output of OR gate 60 (FIG. 1).

URINE MODULE

Figure 9:
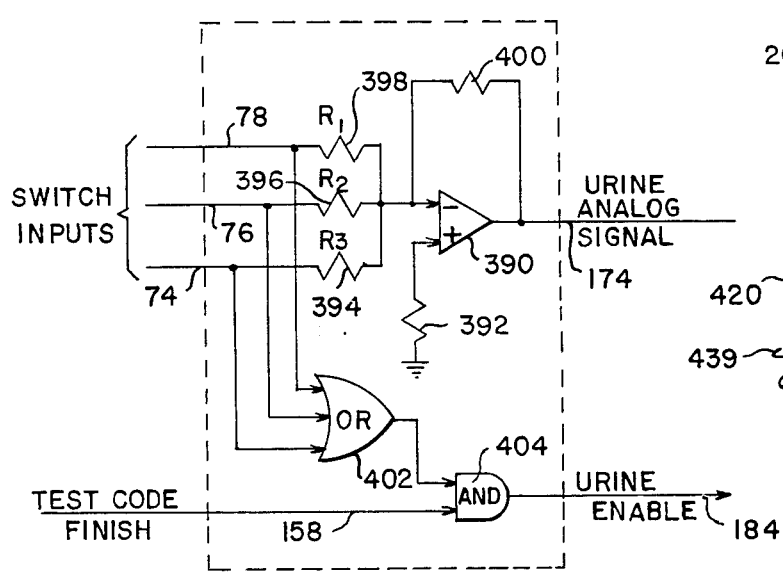
FIG. 9 is a detailed circuit diagram of a urine module incorporated in the system of FIG. 1.

Referring to FIG. 9, urine module 80 includes an operational amplifier 390 having its non-inverting input connected to ground by a resister 392. Input lines 74, 76 and 78 are connected to the inverting input of the operational amplifier by a set of weighted resistances 394, 396 and 398, respectively. A feed-back resistor 400 is provided between the output of operational amplifier 390 and its inverting input. The operational amplifier produces a "Urine Analog" signal in the form of a DC voltage having a magnitude determined by which one of input lines 74, 76 and 78 is actuated.

In addition, input lines 74, 76 and 78 are coupled to the inputs of an OR gate 402 having its output coupled to the first input of an AND gate 404. The second input of AND gate 404 is connected to conductor 158 to respond to the "Test Code Finish" signal produced by the control logic circuit. Upon actuating of any one of input lines 74, 76 and 78 and occurrence of the "Test Code Finish" signal, AND gate 404 produces a "Urine Enable" signal which is applied to select line 184 (FIG. 1) of the multiplexer circuit.

BODY MEASURING UNIT

Figure 10:
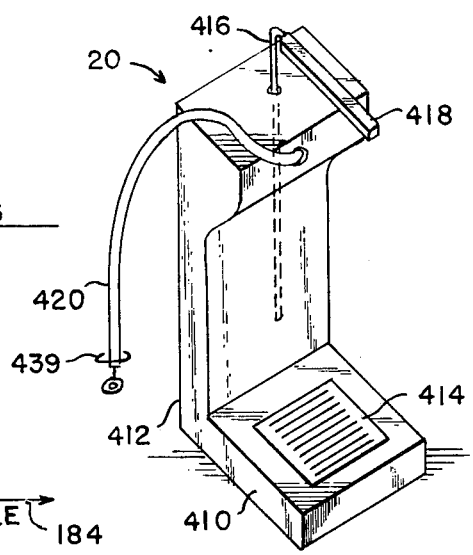
FIG. 10 illustrates an example of a body measuring unit for measuring height, weight, and girth of the human body which may be used in the system of FIG. 1.

Referring to FIG. 10, body measuring unit 20 is preferably embodied as a floor standing unit including a base porton 410 and an upright portion 412. Base portion 410 includes a built-in weight platform 414. In addition, a vertically adjustable height bar 416 including a head rest 418 and a girth measuring device 420 comprising a flexible sheath and tape are mounted at the front of upright portion 412 of the body measuring unit.

Figure 11:
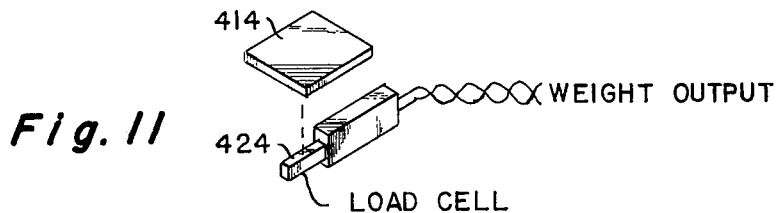
FIG. 11 illustrates a weight platform and load cell of the body measuring unit of FIG. 10 used to perform a weight measurement.

As indicated in FIG. 11, weight platform 414 is mechanically coupled by a suitable linkage (not shown) to a load cell 424, e.g., a piezoelectric cell, responsive to applied stress to produce a linear voltage output proportional to the weight on the platform. The output voltage produced by load cell 424 is applied to buffer amplifier 24 (FIG. 1) to produce the "Weight Analog" signa having a voltage level proportional to the weight of the client on platform 414.

Figure 12:
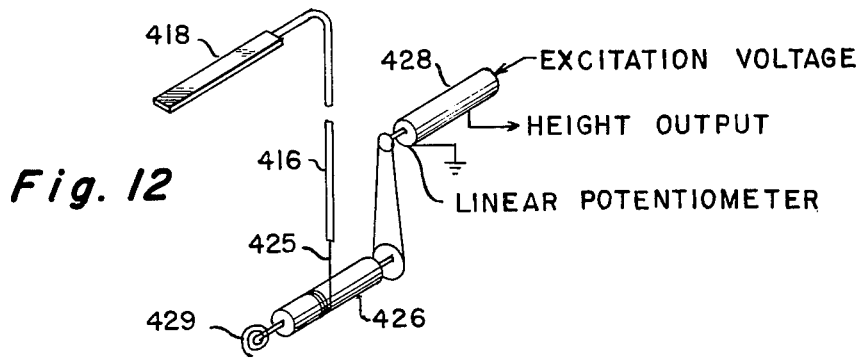
FIG. 12 illustrates an adjustable height bar and linear potentiometer of the body measuring unit of FIG. 10 used to perform a height measurement.

Referring to FIG. 12, adjustable height bar 416 is provided with a flexible cord 425 at its lower end wound on a rotatable drum 426. The drum is coupled to a linear potentiometer 428 by a belt and pulley arrangement for response to rotation of the drum upon vertical movement of the height bar. A constant tension rewind spring 429 is connected to rotatable drum 426 to exert a rewind force on the drum. For example, a linear potentiometer such as T.R.W. Type 7500 is suitable for use with the adjustable height bar. The linear potentiometer produces an output voltage linearly proportional to the vertical position of the height bar. This output signal is applied to buffer amplifier 22

(FIG. 1) to produce the "Height Analog" signal having a voltage level proportional to the height of the client.

Figure 13:
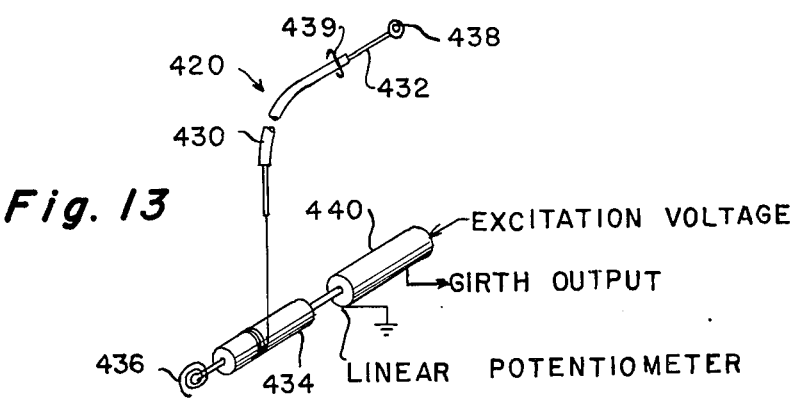
FIG. 13 illustrates an adjustable girth cord and linear potentionometer of the body measuring unit of FIG. 10 used to perform a girth measurement.

Referring to FIG. 13, girth measuring device 420 includes a flexible sheath 430 and an adjustable girth cord 432 slidably received within the sheath. Cord 432 is wound on a rotatable drum 434 connected to a constant tension rewind spring 436 to normally retract the cord into sheath 430. The free end of girth cord 432 includes an enlarged ring 438 to prevent the cord from being completely retracted into the sheat. A suitable connector hook 439 is provided at the free end of sheath 430 to allow ring 438 to be fastened to the sheat after it is extended.

A linear potentiometer 440, e.g., T.R.W. Type 7500, is coupled to drum 434 for response to rotation of the drum upon movement of the girth cord. The linear potentiometer produces a voltage output linearly proportional to the position of girth cord 432 upon extension of the girth cord from the sheath. The output voltage produced by the potentiometer is applied to buffer amplifier 26 (FIG. 1) to produce a "Girth Analog" signal having a voltage level proportional to the girth of the patient being measured.

When the operator desires to perform height, weight and girth measurements, the client is asked to stand on weight platform 414. Then, height bar 416 is raised to place head rest 418 on top of the client's head. Next, the free end of girth measurement device 420 is placed adjacent to the body area, e.g., waist, to be measured and girth cord 432 is extended from the end of the sheath, wrapped around the client's waist, and fastened to the end of the sheath.

Load cell 424 and potentiometers 426 and 430 produce output signals which are applied to the buffer amplifiers 24, 22, and 26, respectively, to produce the "Height Analog" signal, "Weight Analog" signal and "Girth Analog" signal. As explaned above, upon actuation of HWG switch 36, these signals are converted into digital form and recorded in succession on the tape cassette after the unique code signal is recorded.

Upon completion of the height,, weight and waist measurements, the girth cord is unfastened from the end of sheath 430 and the free end of girth measurement device 20 is moved adjacent to the next body area, e.g., chest, to be measured. Girth cord 432 is again extended from the end of the sheath, wrapped around the client's chest, and fastened to the end of the sheath.

The client is asked to inhale and hold while the operator actuates CHEST switch 46. As explained above, upon actuation of the CHEST switch, the unique code signal corresponding to this measurement is recorded on the tape cassette followed by the digital data signal derived from the "Girth Analog" signal produced by potentiometer 430 and buffer amplifier 26. Subsequently, the client is instructed to exhale and CHEST switch 46 is again actuated. As a result, a second code signal and a chest measurement corresponding to the exhaled chest dimension are recorded. After the 2 chest measurements are completed, the operator removes the girth cord from the client's chest.

BLOOD PRESSURE MONITOR

Figure 14:
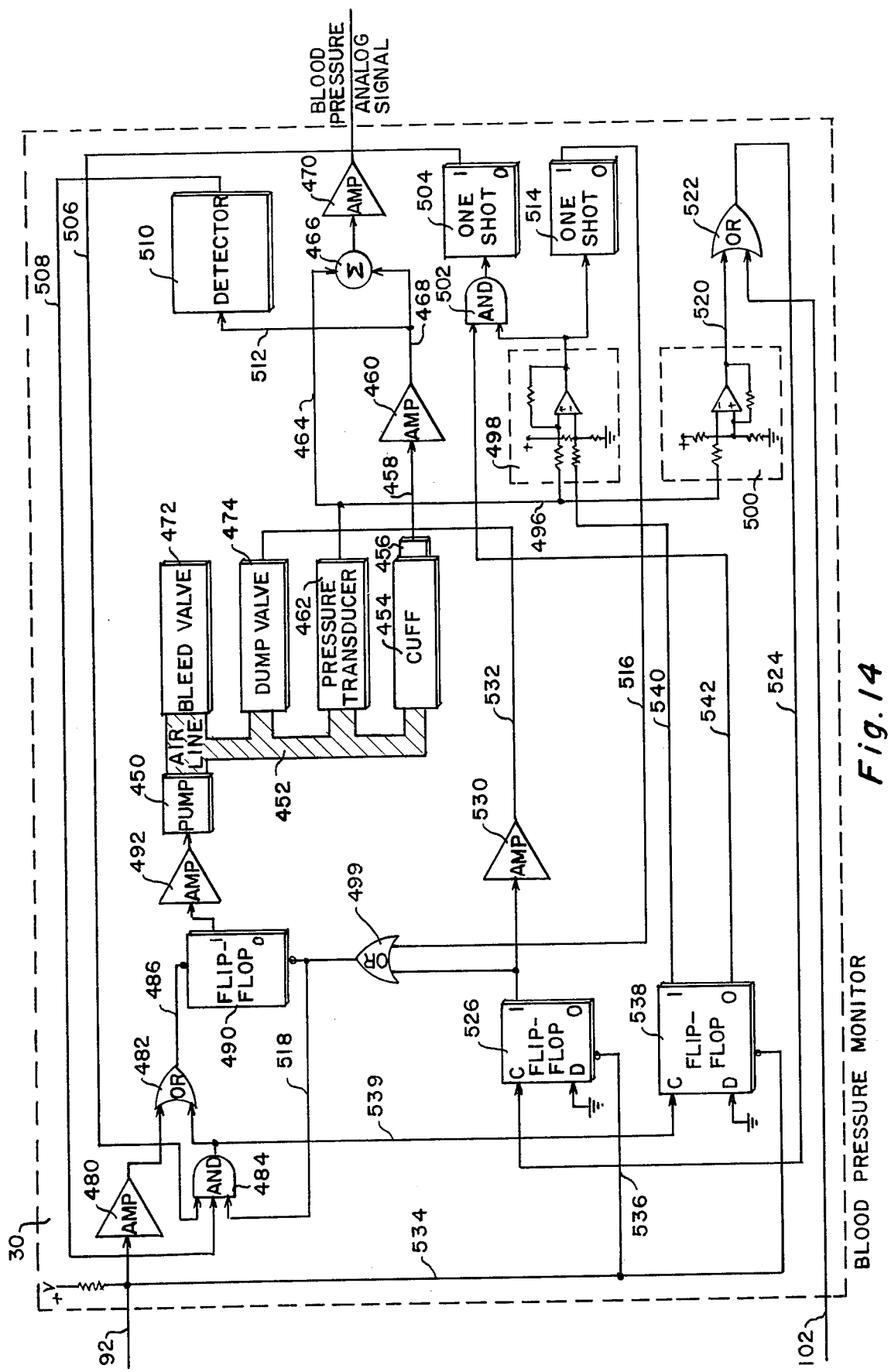
FIG. 14 is a more detailed circuit diagram of a blood pressure monitor incorporated in the system of FIG. 1.

Referring to FIG. 14, blood pressure monitor 30 includes an air pump 450 for supplying air under pressure via an air line 452 in an inflatable cuff 454 supporting a microphone pickup 456 for sensing Korotkoff sounds. The output of microphone pickup 456 is coupled by a conductor 458 to a linear amplifier 460. A pressure transducer 462 senses the pressure in air line 452 and produces a voltage output proportional to the air pressure. The output of pressure transducer 462 is coupled by a conductor 464 to a summation circuit 466 which also receives the output of amplifier 460 via a conductor 468. The combined output of summation circuit 466 is applied to a buffer amplifier 470 which produces the blood pressure analog signal applied to input line 175 (FIG. 2) of the multiplexer circuit.

The blood pressure monitor also includes a bleed valve 472 coupled to air line 452 to allow gradual deflation of the cuff. In addition, a dump valve 474 is provided to allow the cuff to be rapidly deflated.

The operation of pump 450 is controlled by an input circuit coupled to conductor 92 which responds to actuation of BLOOD PRESS switch 88. The input circuit includes an amplifier 480 having its input coupled to conductor 92 and its output coupled to a first input of an OR gate 482. A second input of OR gate 482 is coupled to the output of an AND gate 484. The output of OR gate 482 is coupled to a preset input of a flip-flop 490 having one of its data outputs coupled to an amplifier 492 which serves as a driver for pump 450. Flip-flop 490 includes a clear input coupled to the output of an OR gate 494.

The output of pressure transducer 462 is also coupled by a conductor 496 to a first threshold detector 498 adapted to detect a predetermined high pressure level and a second threshold detector 500 adapted to detect a predetermined low pressure level. The output of threshold detector 498 is gated via an AND gate 502 to a first one-shot circuit 504 having its output coupled by a conductor 506 to a first input of AND gate 484. A second input of AND gate 484 is coupled by a conductor 508 to the output of a Korotkoff sound detector 510 coupled to the output of amplifier 460 by a conductor 512. The output of threshold detector 498 is also applied to a second one-shot circuit 514 having its output coupled by a conductor 516 to a first input of OR gate 494. The output of OR gate 494 is connected by a conductor 518 to a third input of AND gate 484.

The output of threshold detector 500 is coupled by a conductor 520 to a first input of an OR gate 522 having its output coupled by a conductor 524 to a first data input of a flip-flop 526. A second data input of flip-flop 526 is grounded. A data output 1 of flip-flop 526 is coupled via a conductor 528 to an amplifier 530 which is connected by a conductor 532 to dump valve 474. The data output of flip-flop 526 is also coupled by conductor 528 to a second input of OR gate 494. OR gate 522 includes a second input connected to conductor 102 which responds to actuation of B.P. DUMP switch 100.

Input conductor 92 is connected by conductors 534 and 536 to the clear input of flip-flop 526. A flip-flop 538 has its clear input coupled by conductor 534 to input conductor 92. Flip-flop 538 also includes a first data input coupled to the output of AND gate 484 by a conductor 539 and a second data input coupled to ground. A first data output 1 of flip-flop 538 is connected by conductor 540 to threshold detector circuit 498. A second data output 0 of flip-flop 538 is connected by a conductor 542 to an enable input of AND gate 502.

When it is desired to take a blood pressure reading, the operator places the inflatable cuff around the upper arm of the client. Next, the operator depresses BLOOD PRESS switch 88 to apply a control signal via conductor 90 to input line 94 of the control logic circuit to initiate a "Test Code" signal which is recorded on the magnetic tape cassette to identify a blood pressure reading.

Referring to FIG. 14, the control signal initiated upon actuation of the BLOOD PRESS switch is applied by conductor 92, amplifier 480 and OR gate 42 to the preset input of flip-flop 490 to actuate amplifier 492 to drive pump 450. Simultaneously, the control signal is applied via conductors 534 and 536 to the clear inputs of flip-flops 526 and 538. Each flip-flop is reset to its 0 state. The signal at the 0 output of flip-flop 538 is applied to conductor 542 to enable AND gate 502. The absence of a signal at the 1 output of flip-flop 538 sets threshold detector 498 to detect a first predetermined pressure, e.g., 160 mm-Hg.

When pump 450 inflates cuff 454 to the predetermined pressure, i.e., 160 mm-Hg., threshold detector 498 produces an output which is applied to one-shot circuit 514. The one-shot circuit produces an output pulse having a predetermined duration, e.g., 4 seconds, which is applied to the clear input of flip-flop 490 via OR gate 494 to reset the flip-flop and terminate the operation of pump 450. Thereafter, the cuff is gradually deflated at a predetermined rate, e.g., 2.5 mm-Hg./sec., by bleed valve 472.

The output signal produced by detector circuit 498 upon inflation of cuff 454 to the predetermined pressure, i.e., 160 mm-Hg., is also applied by enabled AND gate 502 to one-shot circuit 504. the one-shot circuit produces an output signal for a predetermined time, e.g., 4 seconds, which enables the first input of AND gate 484 via conductor 506. The third input of AND gate 484 is also enabled by the output of one-shot circuit 514 via conductor 516, OR gate 494, and conductor 518. If a Korotkoff sound is detected within the predetermined interval established by one-shot circuits 504 and 514, detector 510 produces an output signal which is applied via conductor 508 to actuate AND gate 484. The AND gate produces an output signal which is applied to the preset input of flip-flop 490 via OR gate 482 to again actuate amplifier 492 to drive pump 450. The output signal produced by AND gate 484 is also applied via conductor 539 to the first data input of flip-flop 538 to set the flip-flop to its 1 state. The signal produced at output 1 of flip-flop 538 is applied via conductor 540 to threshold detector circuit 498 to set the detector circuit to respond to a higher predetermined pressure level, e.g., 230 mm-Hg. In addition, the signal at output 0 of flip-flop 538 is applied as an inhibit signal to AND gate 502 by conductor 542.

When pump 450 inflates cuff 454 to the higher predetermined pressure level, i.e., 230 mm-Hg., threshold detector circuit 498 produces an output signal to operate one-shot circuit 514. The one-shot circuit produces an output pulse for the predetermined time which is applied to the clear input of flip-flop 490 via conductor 526 and OR gate 494 to terminate operation of pump 450. Subsequently, cuff 454 is gradually deflated by bleed valve 472 at the predetermined rate, e.g., 2.5 mm-Hg./sec.

The output signals produced by pressure transducer 462 and microphone pick-up 456 are combined by summation circuit 466 and applied to amplifier 470 to produce the blood pressure analog signal recorded on the magnetic tape cassette. The appearance of Korotkoff sounds in the recorded signal enable the diastolic and systolic blood pressures to be determined.

Finally, when the pressure in cuff 454 drops to a predetermined lower level, e.g., 60 mm-Hg., threshold detector circuit 500 is actuated to apply an output signal to OR gate 522 to reset flip-flop 526 via conductor 524. The output signal produced by flip-flop 526 is applied to amplifier 530 to actuate dump valve 474 to rapidly deflate the cuff.

At any time in the operation of blood pressure monitor 30, the operator can activate dump valve 474 by depressing B.P. DUMP switch 100 to apply a control signal via conductor 102 to OR gate 522. The output signal produced by OR gate 522 is applied to flip-flop 526 via conductor 524 to reset the flip-flop and operate dump valve 474 to deflate the cuff.

ELECTROCARDIOGRAM UNIT

Figure 15:
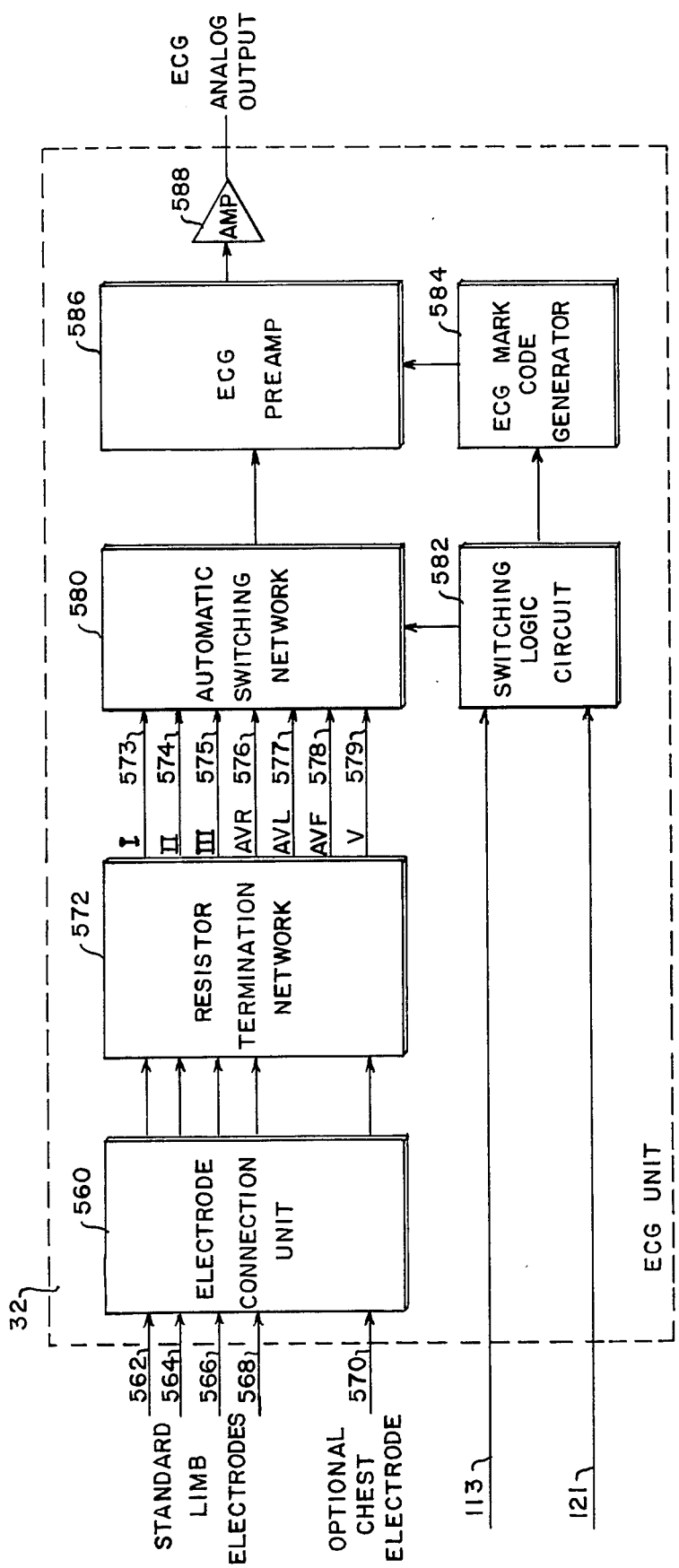
FIG. 15 is a more detailed circuit diagram of an electrocardiogram unit incorporated in the system of FIG. 1.

Referring to FIG. 15, electrocardiogram unit 32 includes an electrode connection unit 560 for connecting a set of standard limb electeodes 562, 564, 566 and 568 and an optional chest electrode 570 to a resistor termination network 572, e.g., a Wilson network. The resistor termination network functions as a summing device to provide the standard ECG leads I, II, III, AVR, AVL and AVF, designated 573–578, respectively, and an additional lead V, designated 579, to provide chest readings. Standard ECG leads 573–578 and lead 579 are applied to an automatic switching network 580 which functions to automatically apply the inputs on these leads in sequence to the output of the automatic switching network.

A switching logic circuit 582 controls the operation of automatic switching network 580 in response to control signals applied to conductors 113 and 121 which respond to actuation of ECG switch 104 and OPT ECG switch 114, respectively. Switching logic circuit 582 also controls an ECG mark code generator 584 which produces a series of different pulse code signals which uniquely identify the various ECG leads. The pulse code signals produced by ECG mark code generator 584 and the analog data signals from the ECG leads produced by automatic switching network 580 are applied to a preamplifier circuit 586 having its output applied to a buffer amplifier 588 which produces the ECG analog signal.

When it is desired to perform an electrocardiogram test, the operator attaches standard limb electrodes 562, 564, 566 and 568 to the arms and legs of the client. Next, the operator depresses ECG switch 104 (FIG. 1) to initiate operation of control logic circuit 34 to produce a unique "Test Code" signal to indicate the performance of an electrocardiogram test. After the "Test Code" signal is recorded, multiplexer circuit 170 (FIG. 2) is operated to respond to the ECG analog signal produced by electrocardiogram unit 32.

The control signal produced upon actuation of ECG switch 104 is also applied via conductor 113 to switching logic circuit 582 (FIG. 15) to initiate operation of automatic switching network 580 and ECG mark code generator 584. The ECG mark code generator produces a unique pulse code signal which is recorded on the magnetic tape cassette to designate a reading from standard ECG lead I. Immediately following the pulse code signal, the analog data signal from standard ECG lead I is recorded on the tape cassette. Thereafter, ECG mark code generator 584 produces unique pulse code signals to identify the other standard ECG leads and the analog data signals from the other leads are recorded on the tape immediately following the corresponding pulse code signals.

If it is desired to perform an optional ECG test with the chest electrode, the operator positions the chest electrode on the client's chest and depresses OPT ECG switch 114 (FIG. 1) to initiate a control signal via conductors 116 and 118 to control logic circuit 34. A "Test Code" signal produced by the control logic circuit to indicate an electrocardiogram test is recorded on the magnetic tape cassette. The control signal produced upon actuation of OPT ECG switch 114 is also applied via conductor 121 to switching logic circuit 582 (FIG. 15). The switching logic circuit operates ECG mark code generator 584 to produce a unique pulse code signal to indicate a chest electrode reading which is recorded on the magnetic tape cassette. Immediately following the pulse code signal, the analog data signal produced by automatic switching network 580 is recorded. Subsequently, the operator positions the chest electrode at different positions on the client's chest and depresses the OPT ECG switch each time an ECG chest reading is desired.

Since the same pulse code signal is generated for each chest reading, regardless of the position of the chest electrode, it is necessary for the operator to record oral information on the magnetic tape cassette to designate the various chest positions. Thus, it is contemplated that, prior to actuation of the OPT ECG switch for a chest reading, the operator can depress the TALK switch and orally record the necessary information via the voice recording arrangement.

TRANSCRIPTION OF INFORMATION ON MAGNETIC TAPE CASSETTE

A suitable transcriber, which forms no part of the present invention, can be provided to transcribe the information on the magnetic tape cassette into appropriate form for analysis at a central insurance facility. Preferably, the transcriber automatically determines whether the recorded information consists of data or voice signals and provides a hard copy output, e.g., strip chart and printer, for all data information and a speaker output for all voice information.

ALTERNATIVE EMBODIMENT

An alternative embodiment of the system can be arranged to record the "Test Code" and data signals in the form of varying audio frequency signals instead of the digital form described above. The alternative embodiment is substantially identical to the system previously described except that the analog signals produced by the multiplexer, instead of being digitized through an analog to digital converter and recorded in the form of digital code and data signals, is applied to a voltage controlled oscillator for conversion into different audio frequency signals to be recorded on channel 1 of the magnetic tape cassette. In addition, it is not necessary for a clock with sync signal to be recorded on channel 2 for the tape cassette.

Referring to FIG. 2, in the alternative embodiment, clock and sync circuit 149 and analog to digital converter 210 are eliminated. A voltage controlled oscillator is connected between output 188 of multiplexer 170 and conductor 216 coupled to gate circuit 218. The gate circuit allows either the varying audio frequency signals produced by the voltage controlled oscillator or the voice input from the voice recording arrangement to be recorded on channel 1 of the magnetic tape cassette.

The invention in its broader aspects is not limited to the specific details shown and described, and moficiations may be made in the details of the system for sensing and recording medical information without departing from the principles of the present invention.

What is claimed is:

1. A system for measuring and recording various characteristics relating to the human body on a magnetic tape cassette, comprising:
    an anthropometer for measuring height, weight and girth of the human body;
    a blood pressure monitor including a cuff and microphone pickup mounted on said cuff for sensing the sounds produced by pulsations of the blood stream;
    an electrocardiogram unit comprising a plurality of input electrodes for connection to the limbs of the human body and a sensing circuit responsive to said output electrodes for providing the standard electrocardiogram leads;
    each of said anthropometer, blood pressure monitor and electrocardiogram unit producing analog data signals representative of the various mesurements taken;
    a plurality of controls for selectively actuating said anthropometer, blood pressure monitor, and electrocardiogram unit;
    control means including a test code generator responsive to actuation of said controls for producing different test code signals corresponding to the various measurements to be performed;
    an analog to digital converter for converting said test code signals and said analog data signals into digital code signal and digital data signals, respectively;
    multiplexer means responsive to said test code signals for selectively supplying said analog data signals from said anthropometer, blood pressure monitor and electrocardiogram unit to said analog to digital converter; and
    means for recording said digital code signals and said digital data signals produced by said analog to digital converter in a predetermined relationship on a magnetic tape cassette.

2. The system of claim 1, which includes a voice recording arrangement comprising:
    a microphone;
    an amplifier coupled to said microphone;
    a multiplexer having a first input connected to the amplifier output, a second input connected to the output of said analog to digital converter, and an outpt connected to said recorder;
    a selector circuit for operating said multiplexer;
    a manually operable control for actuating said selector circuit to operate said multiplexer to connect its first input to said recorder;
    said control means normally applying an inhibit signal to said selector circuit for operating said multiplexer to connect its second input to said recoder.

3. The system of claim 1, which includes:
    a urine module for producing different analog signals to indicate the results of a urine test; and
    a plurality of manually operable controls connected to said module for operating said module to generate an analog data signal representative of the test result.

4. The system of claim 1, which includes:

a plurality of prompt lights operable in succession to indicate a predetermined sequence of the characteristics to be sensed and recorded.

5. The system of claim 1, which includes:

means rendered operable upon actuation of any one of said controls for inhibiting the operation of the remainder of said controls until the measurement corresponding to said one control is recorded.

6. The system of claim 1, including means responsive to actuation of one of said controls for operating said multiplex means to sequentially supply the analog signals representing height, weight and girth to said analog to digital converter.

7. The system of claim 1, wherein the blood pressure monitor includes:

an inflatable cuff;

means responsive to the actuation of one of said controls for inflating the cuff to a predetermined pressure;

means for subsequently deflating said cuff at a predetermined rate; and means responsive to the detection of a Korotkoff sound for reinflating said cuff to a predetermined pressure whereafter deflation of said cuff continues at the same predetermined rate.

8. The system of claim 1, wherein the electrocardiogram unit includes:

an optional chest electrode; and a resistor summing network responsive to the signals applied to said electrodes for providing the standard electrocardiogram leads.

* * * * *

UNITED STATES PATENT AND TRADEMARK OFFICE
CERTIFICATE OF CORRECTION

PATENT NO. : 4,033,336
DATED : July 5, 1977
INVENTOR(S) : Frank H. Murawski et al It is certified that error appears in the above-identified patent and that said Letters Patent are hereby corrected as shown below:

Column 22, line 20, "output" should read --input--.

Column 22, line 24, "mesurements" should read --measurements--.

Column 22, line 53, "outpt" should read --output--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*